United States Patent
Krekeler

(10) Patent No.: US 10,668,073 B2
(45) Date of Patent: Jun. 2, 2020

(54) PHARMACEUTICAL COMPOSITION CONTAINING 8-[(3R)-3-AMINO-1-PIPERIDINYL]-7-(2-BUTYN-1-YL)-3,7-DIHYDRO-3-METHYL-1-[4-METHYL-2-QUINAZOLINYL)METHYL]-1H-PURINE-2,6-DIONE OR A PHARMACEUTICALLY ACCEPTABLE SALT THEREOF

(71) Applicant: HEXAL AG, Holzkirchen (DE)

(72) Inventor: Andreas Krekeler, Holzkirchen (DE)

(73) Assignee: HEXAL AG, Holzkirchen (DE)

( * ) Notice: Subject to any disclaimer, the term of this patent is extended or adjusted under 35 U.S.C. 154(b) by 0 days.

(21) Appl. No.: 15/767,131

(22) PCT Filed: Oct. 7, 2016

(86) PCT No.: PCT/EP2016/073952
§ 371 (c)(1),
(2) Date: Apr. 9, 2018

(87) PCT Pub. No.: WO2017/060398
PCT Pub. Date: Apr. 13, 2017

(65) Prior Publication Data
US 2018/0243310 A1  Aug. 30, 2018

(30) Foreign Application Priority Data
Oct. 9, 2015 (EP) ................................ 15189208

(51) Int. Cl.
| | |
|---|---|
| *A61K 31/522* | (2006.01) |
| *A61K 9/20* | (2006.01) |
| *A61K 9/16* | (2006.01) |
| *A61K 9/28* | (2006.01) |

(52) U.S. Cl.
CPC .......... *A61K 31/522* (2013.01); *A61K 9/1623* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 9/2095* (2013.01); *A61K 9/2866* (2013.01)

(58) Field of Classification Search
CPC .. A61K 31/522; A61K 9/2866; A61K 9/2027; A61K 9/2054; A61K 9/2018; A61K 9/2013; A61K 9/1623; A61K 9/2095; A61K 9/2059; A61K 9/2009
See application file for complete search history.

(56) References Cited

U.S. PATENT DOCUMENTS

| | | | |
|---|---|---|---|
| 2012/0258170 A1* | 10/2012 | Kruthiventi | C07D 311/28 424/464 |
| 2016/0081937 A1* | 3/2016 | Raneburger | A61K 9/146 514/521 |

FOREIGN PATENT DOCUMENTS

| | | |
|---|---|---|
| EP | 2 848 242 A1 | 3/2015 |
| WO | WO 2004/018468 A2 | 3/2004 |
| WO | WO 2007/128721 A1 | 11/2007 |
| WO | WO 2007/128724 A1 | 11/2007 |
| WO | WO 2014/026939 A1 | 2/2014 |
| WO | WO 2014/193528 A1 | 12/2014 |

OTHER PUBLICATIONS

*The European Pharmacopoeia*, 8th Edition, published Jul. 14, 2013, vol. 1, p. 299, Chapter 2.9.8, "Resistance to Crushing of Tablets", Council of Europe, 67075 Strasbourg Cedex, France, 2013, https://www.edqm.eu.
International Search Report and Written Opinion of the International Search Authority dated Nov. 30, 2016 in PCT/EP2016/073952 filed Oct. 7, 2016.

* cited by examiner

*Primary Examiner* — Snigdha Maewall
(74) *Attorney, Agent, or Firm* — Hershkovitz & Associates, PLLC; Abe Hershkovtiz

(57) ABSTRACT

The present invention relates to a pharmaceutical composition comprising linagliptin or a pharmaceutically acceptable salt thereof as active ingredient, wherein the pharmaceutical composition does not comprise a binder and wherein the pharmaceutical composition is obtained by direct compression.

17 Claims, No Drawings

PHARMACEUTICAL COMPOSITION CONTAINING 8-[(3R)-3-AMINO-1-PIPERIDINYL]-7-(2-BUTYN-1-YL)-3,7-DIHYDRO-3-METHYL-1-[4-METHYL-2-QUINAZOLINYL)METHYL]-1H-PURINE-2,6-DIONE OR A PHARMACEUTICALLY ACCEPTABLE SALT THEREOF

FIELD OF THE INVENTION

The present invention relates to a pharmaceutical composition comprising 8-[(3R)-3-amino-1-piperidinyl]-7-(2-butyn-1-yl)-3,7-dihydro-3-methyl-1-[4-methyl-2-quinazolinyl)methyl]-1H-purine-2,6-dione (linagliptin) or a pharmaceutically acceptable salt of linagliptin, a process for preparing the pharmaceutical composition, and the use of the pharmaceutical composition in the treatment of metabolic disorders, such as type 2 diabetes mellitus.

BACKGROUND OF THE INVENTION

Linagliptin (8-[(3R)-3-amino-1-piperidinyl]-7-(2-butyn-1-yl)-3,7-dihydro-3-methyl-1-[4-methyl-2-quinazolinyl) methyl]-1H-purine-2,6-dione) acts as a dipeptidyl peptidase IV (DPP IV) inhibitor and is currently used in the treatment of type 2 diabetes mellitus.

WO2004/018468 discloses linagliptin, salts thereof, a process for the preparation of linagliptin and its salts, and the use of linagliptin, and its salts for the treatment of certain diseases.

WO2007/128721 describes crystalline forms A, B, C, D, and E of linagliptin and processes for preparing the crystalline forms. It also discloses that linagliptin prepared according to WO2004/018468 is in the form of a mixture of crystalline form A and crystalline form B.

WO2007/128724 discloses a pharmaceutical composition comprising a DPP IV inhibitor compound with an amino group, such as linagliptin or a salt thereof, a first diluent, a second diluent, a binder, a disintegrant and a lubricant.

WO2014/026939 discloses a pharmaceutical composition comprising linagliptin or salts thereof with mannitol, copovidone, and magnesium stearate, a process for the preparation of the pharmaceutical composition, and a container comprising the pharmaceutical composition.

However, there is the need to provide a pharmaceutical composition which can be obtained by a more efficient manufacturing process without the use of solvents and with a low number of process steps. In particular, a low number of excipients should be used to reduce complexity of the process, specifically to reduce the number of manual interventions (adding excipients, mixing steps), to reduce the number of analytical processes to be applied (release analytics for each excipient prior to use) and to reduce overall production costs. The pharmaceutical composition obtained by said more efficient manufacturing process nevertheless needs to have suitable properties allowing handling on an industrial scale in high speed manufacturing equipment and at the same time a fast dissolution in the gastrointestinal tract after administration together with a suitable content uniformity of the active ingredient and a sufficient storage stability. The content uniformity is of special importance because linagliptin is present in a pharmaceutical composition in a low amount of about 0.5 to 5% by weight.

SUMMARY OF THE INVENTION

It was surprisingly found that the above objects are achieved by a pharmaceutical composition comprising linagliptin or a pharmaceutically acceptable salt thereof as active ingredient, wherein the pharmaceutical composition does not comprise a binder and wherein the pharmaceutical composition is obtained by direct compression. It is an unexpected finding that one excipient, the binder, which was previously considered as being a mandatory excipient, can be omitted.

The lower number of excipients compared to prior art processes combined with the omission of any solvents reduces the complexity of the manufacturing process. As a result, the overall production costs for the pharmaceutical composition can be minimized. Surprisingly, it was found that the omission of the binder combined with the use of direct compression for manufacturing the pharmaceutical composition neither negatively influences the dissolution rate nor the content uniformity and allows high speed industrial manufacturing, thus permitting to produce the pharmaceutical composition at low costs.

DETAILED DESCRIPTION OF THE INVENTION

In a first aspect of the invention, it is provided a pharmaceutical composition comprising linagliptin or a pharmaceutically acceptable salt thereof as active ingredient, wherein the pharmaceutical composition does not comprise a binder and wherein the pharmaceutical composition is obtained by direct compression.

A binder, within the meaning of the present invention, is a compound selected from the group consisting of: lactose (including anhydrous lactose and lactose monohydrate), povidone (polyvinylpyrrolidone), copovidone (copolymerisates of vinylpyrrolidone with other vinyl derivatives), hydroxypropyl methylcellulose (HPMC), hydroxypropylcellulose (HPC, including HPC of any substitution grade, in particular low-substituted HPC), pre-gelatinized starch, microcrystalline cellulose, polyethylene glycol and pullulan.

Pharmaceutically acceptable salts of linagliptin are, for example, the salts as defined in WO2010/072776, including the hydrochloride, hydrobromide, benzoate, mesylate, esylate, besylate, tosylate, fumarate, salicylate, glycolate, malonate and gentisate salt, and in particular the benzoate salt as defined in WO2012/152837.

Linagliptin or the pharmaceutically acceptable salt thereof is preferably present in the pharmaceutical composition in an amount of 0.5 to 5% by weight, more preferably 1 to 4% by weight, even more preferably 2 to 3% by weight.

In a second aspect of the invention, it is provided a pharmaceutical composition comprising linagliptin or a pharmaceutically acceptable salt thereof as active ingredient, wherein the pharmaceutical composition does not comprise a binder, wherein the pharmaceutical composition is obtained by direct compression, and wherein the pharmaceutical composition comprises additionally one or more excipients selected from diluents, disintegrants and lubricants.

The one or more diluents are preferably present in the pharmaceutical composition in an amount of 60 to 99.5% by weight, more preferably 75 to 99.5% by weight, even more preferably 85 to 99.5% by weight, most preferably 95 to 99.5% by weight of the pharmaceutical composition.

The one or more disintegrants are preferably present in the pharmaceutical composition in an amount of 1 to 15% by weight, more preferably 1 to 10% by weight of the pharmaceutical composition.

The one or more lubricants are preferably present in the pharmaceutical composition in an amount of 0.01 to 5% by weight, more preferably 0.1 to 3% by weight and even more preferably 0.5 to 2% by weight of the pharmaceutical composition.

In a preferred embodiment of the second aspect of the invention, the diluent comprises anhydrous calcium hydrogen phosphate. In an even more preferred embodiment of the second aspect of the invention, anhydrous calcium hydrogen phosphate is the only diluent present in the composition.

The use of anhydrous calcium hydrogen phosphate as diluent is advantageous because of its compaction and flow properties contributing to suitable content uniformity and suitable handling properties during large scale manufacturing by direct compression. Moreover, it does not affect stability of the active ingredient and does not prolong the dissolution of the pharmaceutical composition.

In an alternative preferred embodiment of the second aspect of the invention, the diluent comprises a combination of anhydrous calcium hydrogen phosphate and mannitol. In an even more preferred alternative embodiment of the second aspect of the invention, anhydrous calcium hydrogen phosphate and mannitol are the only diluents present in the composition. The anhydrous calcium hydrogen phosphate is preferably present in the pharmaceutical composition in an amount of 20 to 50% by weight, more preferably 30 to 50% by weight, even more preferably 35 to 45% by weight, based on the combined amount of anhydrous calcium hydrogen phosphate and mannitol. The mannitol is preferably present in the pharmaceutical composition in an amount of 50 to 80% by weight, more preferably 50 to 70% by weight, even more preferably 55 to 65% by weight, based on the combined amount of anhydrous calcium hydrogen phosphate and mannitol.

Using a combination of anhydrous calcium hydrogen phosphate and mannitol has the advantages of good compactability and flowability contributing to suitable content uniformity and suitable handling properties during manufacturing by direct compression. Moreover, neither anhydrous calcium hydrogen phosphate nor mannitol are hygroscopic and they do not negatively influence the stability of the active ingredient. Furthermore, they do not adversely impact the dissolution properties of the pharmaceutical composition.

For some pharmaceutical compositions, such as chewable tablets, orally disintegrating tablets or effervescent tablets, the use of mannitol has the additional advantage that it has a sweet taste and imparts a cooling sensation in the mouth.

In a further embodiment of the second aspect of the invention, the pharmaceutical composition preferably comprises a lubricant selected from magnesium stearate, talc, stearic acid, calcium behenate, calcium stearate and sodium stearyl fumarate. Particularly preferred lubricants are magnesium stearate and sodium stearyl fumarate. The most preferred lubricant is sodium stearyl fumarate.

In a further embodiment of the second aspect of the invention, the pharmaceutical composition preferably comprises a disintegrant selected from starch (such as maize starch), crospovidone, sodium starch glycolate and croscarmellose sodium. More preferably the disintegrant selected is from sodium starch glycolate and croscarmellose sodium.

In a further embodiment of the second aspect of the invention, the pharmaceutical composition, which is obtained by direct compression, preferably comprises, more preferably consists of, linagliptin or a pharmaceutically acceptable salt thereof, anhydrous calcium hydrogen phosphate, a disintegrant selected from sodium starch glycolate and croscarmellose sodium, and a lubricant selected from magnesium stearate and sodium stearyl fumarate.

In a further embodiment of the second aspect of the invention, the pharmaceutical composition, which is obtained by direct compression, preferably comprises, more preferably consists of, linagliptin or a pharmaceutically acceptable salt thereof, anhydrous calcium hydrogen phosphate, crospovidone and sodium stearyl fumarate.

In a further embodiment of the second aspect of the invention, the pharmaceutical composition, which is obtained by direct compression, preferably comprises, more preferably consists of, linagliptin or a pharmaceutically acceptable salt thereof, anhydrous calcium hydrogen phosphate, crospovidone and magnesium stearate.

In a further embodiment of the second aspect of the invention, the pharmaceutical composition, which is obtained by direct compression, preferably comprises, more preferably consists of, linagliptin or a pharmaceutically acceptable salt thereof, anhydrous calcium hydrogen phosphate, maize starch and sodium stearyl fumarate.

In a further embodiment of the second aspect of the invention, the pharmaceutical composition, which is obtained by direct compression, preferably comprises, more preferably consists of, linagliptin or a pharmaceutically acceptable salt thereof, anhydrous calcium hydrogen phosphate, sodium starch glycolate and sodium stearyl fumarate.

In a further embodiment of the second aspect of the invention, the pharmaceutical composition, which is obtained by direct compression, preferably comprises, more preferably consists of, linagliptin or a pharmaceutically acceptable salt thereof, anhydrous calcium hydrogen phosphate, mannitol, maize starch and sodium stearyl fumarate.

In a further embodiment of the second aspect of the invention, the pharmaceutical composition, which is obtained by direct compression, preferably comprises, more preferably consists of, linagliptin or a pharmaceutically acceptable salt thereof, anhydrous calcium hydrogen phosphate, mannitol, maize starch and magnesium stearate.

In a further embodiment of the second aspect of the invention, the pharmaceutical composition, which is obtained by direct compression, preferably comprises, more preferably consists of, linagliptin or a pharmaceutically acceptable salt thereof, anhydrous calcium hydrogen phosphate, mannitol, croscarmellose sodium and magnesium stearate.

In a third aspect of the invention, it is provided a pharmaceutical composition comprising linagliptin or a pharmaceutically acceptable salt thereof as active ingredient, wherein the pharmaceutical composition does not comprise a binder and does not comprise a disintegrant, and wherein the pharmaceutical composition is obtained by direct compression. It has surprisingly been found that the manufacturing process can be further simplified by not only omitting the binder, but by also omitting the disintegrant, two excipients which hitherto have been considered essential. Nevertheless, a stable pharmaceutical composition having suitable handling properties allowing high speed industrial manufacturing by direct compression and showing fast dissolution together with a suitable content uniformity can be obtained.

In a preferred embodiment of the third aspect of the invention, the pharmaceutical composition, which is obtained by direct compression, comprises, more preferably consists of, linagliptin or a pharmaceutically acceptable salt thereof, anhydrous calcium hydrogen phosphate, and magnesium stearate.

In a further embodiment of the third aspect of the invention, the pharmaceutical composition, which is obtained by direct compression, preferably comprises, more preferably consists of, linagliptin or a pharmaceutically acceptable salt thereof, anhydrous calcium hydrogen phosphate, and sodium stearyl fumarate.

In a further embodiment of the third aspect of the invention, the pharmaceutical composition, which is obtained by direct compression, preferably comprises, more preferably consists of, linagliptin or a pharmaceutically acceptable salt thereof, anhydrous calcium hydrogen phosphate, mannitol, and sodium stearyl fumarate.

In a further embodiment of the third aspect of the invention, the pharmaceutical composition, which is obtained by direct compression, preferably comprises, more preferably consists of, linagliptin or a pharmaceutically acceptable salt thereof, anhydrous calcium hydrogen phosphate, mannitol, and magnesium stearate.

In a fourth aspect of the invention, it is provided a pharmaceutical composition comprising linagliptin or a pharmaceutically acceptable salt thereof as active ingredient, wherein the pharmaceutical composition does not comprise a binder, and optionally does not comprise a disintegrant, and wherein the pharmaceutical composition is obtained by direct compression, which pharmaceutical composition is in the form of a tablet, a coated tablet, an effervescent tablet, an orally disintegrating tablet, a chewable tablet or a capsule filled with minitablets.

Preferably, a single dose of the pharmaceutical composition contains 0.1 to 100 mg, preferably 0.5 mg, 1 mg, 2.5 mg, 5 mg or 10 mg, more preferably 5 mg of linagliptin free base or the equivalent amount of the pharmaceutically acceptable salt thereof. A single dose is, for example, a single tablet, a single coated tablet, a single effervescent tablet, a single orally disintegrating tablet, a single chewable tablet or a single capsule filled with minitablets.

In a preferred embodiment of the fourth aspect of the invention, the coating of the coated tablet comprises hydroxypropyl methylcellulose, polyethylene glycol, talc, titanium dioxide, and optionally a colorant. The colorant is, for example, an iron oxide, such as iron oxide red or iron oxide yellow. The coating preferably represents 2 to 10% by weight, more preferably 5 to 10% by weight of the pharmaceutical composition.

In a further embodiment of the fourth aspect of the invention, the pharmaceutical composition is preferably a coated tablet and comprises 5 mg of linagliptin free base or an equivalent amount of the pharmaceutically acceptable salt thereof, comprises anhydrous calcium hydrogen phosphate as diluent and a lubricant selected from magnesium stearate and sodium stearyl fumarate, wherein the pharmaceutical composition does not comprise a binder, and optionally does not comprise a disintegrant, and wherein the pharmaceutical composition is obtained by direct compression.

In a further embodiment of the fourth aspect of the invention, the pharmaceutical composition is preferably a coated tablet and comprises 5 mg of linagliptin free base or an equivalent amount of the pharmaceutically acceptable salt thereof, comprises a combination of mannitol and anhydrous calcium hydrogen phosphate as diluent and a lubricant selected from magnesium stearate and sodium stearyl fumarate, wherein the pharmaceutical composition does not comprise a binder, and optionally does not comprise a disintegrant, and wherein the pharmaceutical composition is obtained by direct compression.

In a fifth aspect of the invention, it is provided a pharmaceutical composition comprising linagliptin as active ingredient, wherein the pharmaceutical composition does not comprise a binder, and optionally does not comprise a disintegrant, wherein the pharmaceutical composition is obtained by direct compression, and wherein the linagliptin is present as amorphous linagliptin, crystalline linagliptin having polymorphic form A, crystalline linagliptin having polymorphic form B and/or crystalline linagliptin having polymorphic form C.

In a preferred embodiment of the fifth aspect of the invention, the linagliptin is present as a mixture of crystalline linagliptin having polymorphic form A and crystalline linagliptin having polymorphic form B.

In an alternative preferred embodiment of the fifth aspect of the invention, the linagliptin is present as amorphous linagliptin.

The polymorphic forms A, B and C can be prepared as described in WO2007/128721. The mixture of crystalline linagliptin having polymorphic form A and crystalline linagliptin having polymorphic form B can be prepared as described in WO2004/018468 or by mixing crystalline linagliptin polymorphic form A with crystalline linagliptin polymorphic form B. Amorphous linagliptin and its preparation is described in WO2014/026939.

In a preferred embodiment of the fifth aspect of the invention, the pharmaceutical composition, which is obtained by direct compression, preferably comprises, more preferably consists of, crystalline linagliptin having polymorphic form A, crystalline linagliptin having polymorphic form B, anhydrous calcium hydrogen phosphate, a disintegrant selected from sodium starch glycolate and croscarmellose sodium, and a lubricant selected from magnesium stearate and sodium stearyl fumarate.

In a further embodiment of the fifth aspect of the invention, the pharmaceutical composition, which is obtained by direct compression, preferably comprises, more preferably consists of, crystalline linagliptin having polymorphic form A, crystalline linagliptin having polymorphic form B, anhydrous calcium hydrogen phosphate, crospovidone and sodium stearyl fumarate.

In a further embodiment of the fifth aspect of the invention, the pharmaceutical composition, which is obtained by direct compression, preferably comprises, more preferably consists of, crystalline linagliptin having polymorphic form A, crystalline linagliptin having polymorphic form B, anhydrous calcium hydrogen phosphate, crospovidone and magnesium stearate.

In a further embodiment of the fifth aspect of the invention, the pharmaceutical composition, which is obtained by direct compression, preferably comprises, more preferably consists of, crystalline linagliptin having polymorphic form A, crystalline linagliptin having polymorphic form B, anhydrous calcium hydrogen phosphate, maize starch and sodium stearyl fumarate.

In a further embodiment of the fifth aspect of the invention, the pharmaceutical composition, which is obtained by direct compression, preferably comprises, more preferably consists of, crystalline linagliptin having polymorphic form A, crystalline linagliptin having polymorphic form B, anhydrous calcium hydrogen phosphate, sodium starch glycolate and sodium stearyl fumarate.

In a further embodiment of the fifth aspect of the invention, the pharmaceutical composition, which is obtained by direct compression, preferably comprises, more preferably consists of, crystalline linagliptin having polymorphic form A, crystalline linagliptin having polymorphic form B, anhydrous calcium hydrogen phosphate, mannitol, maize starch and sodium stearyl fumarate.

In a further embodiment of the fifth aspect of the invention, the pharmaceutical composition, which is obtained by direct compression, preferably comprises, more preferably consists of, crystalline linagliptin having polymorphic form A, crystalline linagliptin having polymorphic form B, anhydrous calcium hydrogen phosphate, mannitol, maize starch and magnesium stearate.

In a further embodiment of the fifth aspect of the invention, the pharmaceutical composition, which is obtained by direct compression, preferably comprises, more preferably consists of, crystalline linagliptin having polymorphic form A, crystalline linagliptin having polymorphic form B, anhydrous calcium hydrogen phosphate, mannitol, croscarmellose sodium and magnesium stearate.

In a sixth aspect of the invention, it is provided a pharmaceutical composition comprising a pharmaceutically acceptable salt of linagliptin as active ingredient, wherein the pharmaceutical composition does not comprise a binder, and optionally does not comprise a disintegrant, wherein the pharmaceutical composition is obtained by direct compression, and wherein the pharmaceutically acceptable salt of linagliptin is crystalline linagliptin benzoate as defined in WO2012/152837, in particular crystalline linagliptin benzoate having an X-ray powder diffraction pattern comprising peaks at 2-theta angles of 8.0±0.2°, 8.7±0.2°, 10.4±0.2°, 12.9±0.2°, 13.8±0.2° and 17.4±0.2° (hereinafter referred to as crystalline linagliptin benzoate form II).

In a preferred embodiment of the sixth aspect of the invention, the pharmaceutical composition, which is obtained by direct compression, comprises, more preferably consists of, crystalline linagliptin benzoate form II, anhydrous calcium hydrogen phosphate, a disintegrant selected from sodium starch glycolate and croscarmellose sodium, and a lubricant selected from magnesium stearate and sodium stearyl fumarate.

In a further embodiment of the sixth aspect of the invention, the pharmaceutical composition, which is obtained by direct compression, preferably comprises, more preferably consists of, crystalline linagliptin benzoate form II, anhydrous calcium hydrogen phosphate, crospovidone and sodium stearyl fumarate.

In a further embodiment of the sixth aspect of the invention, the pharmaceutical composition, which is obtained by direct compression, preferably comprises, more preferably consists of, crystalline linagliptin benzoate form II, anhydrous calcium hydrogen phosphate, crospovidone and magnesium stearate.

In a further embodiment of the sixth aspect of the invention, the pharmaceutical composition, which is obtained by direct compression, preferably comprises, more preferably consists of, crystalline linagliptin benzoate form II, anhydrous calcium hydrogen phosphate, maize starch and sodium stearyl fumarate.

In a further embodiment of the sixth aspect of the invention, the pharmaceutical composition, which is obtained by direct compression, preferably comprises, more preferably consists of, crystalline linagliptin benzoate form II, anhydrous calcium hydrogen phosphate, sodium starch glycolate and sodium stearyl fumarate.

In a further embodiment of the sixth aspect of the invention, the pharmaceutical composition, which is obtained by direct compression, preferably comprises, more preferably consists of, crystalline linagliptin benzoate form II, anhydrous calcium hydrogen phosphate, mannitol, maize starch and sodium stearyl fumarate.

In a further embodiment of the sixth aspect of the invention, the pharmaceutical composition, which is obtained by direct compression, preferably comprises, more preferably consists of, crystalline linagliptin benzoate form II, anhydrous calcium hydrogen phosphate, mannitol, maize starch and magnesium stearate.

In a further embodiment of the sixth aspect of the invention, the pharmaceutical composition, which is obtained by direct compression, preferably comprises, more preferably consists of, crystalline linagliptin benzoate form II, anhydrous calcium hydrogen phosphate, mannitol, croscarmellose sodium and magnesium stearate.

In a seventh aspect of the invention, it is provided a pharmaceutical composition comprising linagliptin or a pharmaceutically acceptable salt thereof as active ingredient, wherein the pharmaceutical composition does not comprise a binder, and optionally does not comprise a disintegrant, wherein the pharmaceutical composition is obtained by direct compression, and wherein the pharmaceutical composition is a tablet and has a tablet hardness in the range of from 60 to 120 N, more preferably 60 to 100 N, even more preferably 70 to 90 N.

The tablet hardness is measured according to the European Pharmacopoeia 8.0 chapter 2.9.8 (resistance to crushing of tablets) with the apparatus Schleuniger Typ 6D 4.11/6D 4.50, wherein the tablets are placed between the jaws in a manner that the force applies to the longest axis of the tablets, where applicable.

In a preferred embodiment of the seventh aspect of the invention, the pharmaceutical composition, which is obtained by direct compression, comprises linagliptin or a pharmaceutically acceptable salt thereof as active ingredient, anhydrous calcium hydrogen phosphate as diluent, and a lubricant selected from magnesium stearate and sodium stearyl fumarate, wherein the pharmaceutical composition does not comprise a binder, and optionally does not comprise a disintegrant, and wherein the pharmaceutical composition is a tablet and has a tablet hardness in the range of from 60 to 120 N, more preferably 60 to 100 N, even more preferably 70 to 90 N.

In a further embodiment of the seventh aspect of the invention, the pharmaceutical composition, which is obtained by direct compression, preferably comprises linagliptin or a pharmaceutically acceptable salt thereof as active ingredient, a combination of anhydrous calcium hydrogen phosphate and mannitol as diluent and a lubricant selected from magnesium stearate and sodium stearyl fumarate, wherein the pharmaceutical composition does not comprise a binder, and optionally does not comprise a disintegrant, and wherein the pharmaceutical composition is a tablet and has a tablet hardness in the range of from 60 to 120 N, more preferably 60 to 100 N, even more preferably 70 to 90 N.

In an eighth aspect of the invention, it is provided a process for preparing a pharmaceutical composition comprising linagliptin or a pharmaceutically acceptable salt thereof as active ingredient, wherein the pharmaceutical composition does not comprise a binder, and optionally does not comprise a disintegrant, which process comprises a direct compression step, and optionally a coating step.

In a preferred embodiment of the eighth aspect of the invention, the process comprises mixing linagliptin, or a pharmaceutically acceptable salt thereof, with a diluent, a lubricant, and optionally a disintegrant, and directly compressing the blend.

In a further embodiment of the eighth aspect of the invention, the process preferably comprises the following steps:
  I) blending linagliptin, or a pharmaceutically acceptable salt thereof, and the excipients, except the lubricant;

II) lubricating the blend using the lubricant;
III) directly compressing the blend; IV) optionally, applying a coating.

In a further embodiment of the eighth aspect of the invention, the process preferably comprises the following steps:
I) blending linagliptin, or a pharmaceutically acceptable salt thereof, with the diluent(s), and optionally the disintegrant(s);
II) lubricating the blend using the lubricant;
III) directly compressing the blend;
IV) optionally, applying a coating.

In a ninth aspect of the invention, it is provided a pharmaceutical composition comprising linagliptin or a pharmaceutically acceptable salt thereof as active ingredient, wherein the pharmaceutical composition does not comprise a binder, and optionally does not comprise a disintegrant, wherein the pharmaceutical composition is obtained by direct compression, and wherein the pharmaceutical composition comprises a further active ingredient selected from active ingredients that lower the blood sugar level, active ingredients that lower the lipid level in the blood, active ingredients that raise the HDL (high density lipoprotein) level in the blood, active ingredients that lower blood pressure, active ingredients indicated in the treatment of obesity, and active ingredients indicated in the treatment of atherosclerosis.

In a preferred embodiment of the ninth aspect of the invention, the further active ingredient that lowers the blood sugar level is selected from biguanides, thiazolidinediones, sulfonylureas, glinides, inhibitors of alpha-glycosidase, GLP-1 (glucagon-like peptide 1), GLP-1 analogues, SGLT-2 (sodium glucose co-transporter-2) inhibitors, insulin, insulin analogues and mixtures thereof.

In a further embodiment of the ninth aspect of the invention, the preferred further active ingredient is selected from metformin hydrochloride and empagliflozin, with metformin hydrochloride being particularly preferred.

In a further embodiment of the ninth aspect of the invention, a preferred pharmaceutical composition, which is obtained by direct compression, comprises, more preferably consists of, linagliptin or a pharmaceutically acceptable salt thereof, metformin or a pharmaceutically acceptable salt thereof, anhydrous calcium hydrogen phosphate, sodium stearyl fumarate and croscarmellose sodium.

In a further embodiment of the ninth aspect of the invention, a preferred pharmaceutical composition, which is obtained by direct compression, comprises, more preferably consists of, linagliptin or a pharmaceutically acceptable salt thereof, metformin or a pharmaceutically acceptable salt thereof, anhydrous calcium hydrogen phosphate and sodium stearyl fumarate.

The pharmaceutical composition according to the invention can be used in the treatment of metabolic disorders including pre-diabetes, glucose intolerance, pathological fasting glucose, hyperglycemia, type II diabetes mellitus, gestational diabetes, disorders associated with type II diabetes mellitus or gestational diabetes, such as wound healing disorders, obesity, diabetic foot, diabetes-associated ulcer, diabetic hyperlipidemia, diabetic dyslipidemia. The pharmaceutical composition according to the invention can further be used for supporting allograft transplantation, in particular, the transplantation of islets of Langerhans or beta cells. The pharmaceutical composition according to the invention can also be used for the treatment of osteoporosis, rheumatoid arthritis, osteoarthritis, neurotraumatic diseases, pain, migraine, acne, proliferative skin diseases, such as psoriasis, hyperproliferative diseases, cardiac hypertrophy, cirrhosis, and fibromatoses.

EXAMPLES

Example 1

| Ingredient | Amount (mg/tablet) |
| --- | --- |
| Linagliptin | 5.0 |
| Anhydrous calcium hydrogen phosphate | 167.8 |
| Crospovidone | 4.5 |
| Sodium stearyl fumarate | 2.7 |
| Sum | 180 |

Linagliptin, anhydrous calcium hydrogen phosphate and crospovidone are dry mixed in a rotary drum mixer for about 10 min. The sodium stearyl fumarate is added and the components are mixed for about 1 min in a rotary drum mixer. The mixture is finally compressed into tablet cores using a Kilian rotary tablet press.

Example 2

| Ingredient | Amount (mg/tablet) |
| --- | --- |
| Linagliptin | 5.0 |
| Anhydrous calcium hydrogen phosphate | 167.8 |
| Crospovidone | 4.5 |
| Magnesium stearate | 2.7 |
| Sum | 180 |

Linagliptin, anhydrous calcium hydrogen phosphate and crospovidone are dry mixed in a rotary drum mixer for about 10 min. The magnesium stearate is added and the components are mixed for about 1 min in a rotary drum mixer. The mixture is finally compressed into tablet cores using a Kilian rotary tablet press.

Example 3

| Ingredient | Amount (mg/tablet) |
| --- | --- |
| Linagliptin | 5.0 |
| Anhydrous calcium hydrogen phosphate | 154.0 |
| Maize starch | 18.0 |
| Sodium stearyl fumarate | 2.7 |
| Sum | 180 |

Linagliptin, anhydrous calcium hydrogen phosphate and maize starch are dry mixed in a rotary drum mixer for about 10 min. The sodium stearyl fumarate is added and the components are mixed for about 1 min in a rotary drum mixer. The mixture is finally compressed into tablet cores using a Kilian rotary tablet press.

Example 4

| Ingredient | Amount (mg/tablet) |
| --- | --- |
| Linagliptin | 5.0 |
| Anhydrous calcium hydrogen phosphate | 167.8 |
| Sodium starch glycolate | 4.5 |
| Sodium stearyl fumarate | 2.7 |
| Sum | 180 |

Linagliptin, anhydrous calcium hydrogen phosphate and sodium starch glycolate are dry mixed in a rotary drum mixer for about 10 min. The sodium stearyl fumarate is added and the components are mixed for about 1 min in a rotary drum mixer. The mixture is finally compressed into tablet cores using a Kilian rotary tablet press.

Example 5

| Ingredient | Amount (mg/tablet) |
| --- | --- |
| Linagliptin | 5.0 |
| Anhydrous calcium hydrogen phosphate | 67.8 |
| Mannitol | 100.0 |
| Sodium starch glycolate | 4.5 |
| Sodium stearyl fumarate | 2.7 |
| Sum | 180 |

Linagliptin, anhydrous calcium hydrogen phosphate, mannitol and sodium starch glycolate are dry mixed in a rotary drum mixer for about 10 min. The sodium stearyl fumarate is added and the components are mixed for about 1 min in a rotary drum mixer. The mixture is finally compressed into tablet cores using a Kilian rotary tablet press.

Example 6

| Ingredient | Amount (mg/tablet) |
| --- | --- |
| Linagliptin | 5.0 |
| Anhydrous calcium hydrogen phosphate | 67.8 |
| Mannitol | 100.0 |
| Sodium starch glycolate | 4.5 |
| Magnesium stearate | 2.7 |
| Sum | 180 |

Linagliptin, anhydrous calcium hydrogen phosphate, mannitol and sodium starch glycolate are dry mixed in a rotary drum mixer for about 10 min. The magnesium stearate is added and the components are mixed for about 1 min in a rotary drum mixer. The mixture is finally compressed into tablet cores using a Kilian rotary tablet press.

Example 7

| Ingredient | Amount (mg/tablet) |
| --- | --- |
| Linagliptin | 5.0 |
| Anhydrous calcium hydrogen phosphate | 67.8 |
| Mannitol | 100.0 |
| Croscarmellose sodium | 4.5 |
| Magnesium stearate | 2.7 |
| Sum | 180 |

Linagliptin, anhydrous calcium hydrogen phosphate, mannitol and croscarmellose sodium are dry mixed in a rotary drum mixer for about 10 min. The magnesium stearate is added and the components are mixed for about 1 min in a rotary drum mixer. The mixture is finally compressed into tablet cores using a Kilian rotary tablet press.

Example 8

| Ingredient | Amount (mg/tablet) |
| --- | --- |
| Linagliptin | 5.0 |
| Anhydrous calcium hydrogen phosphate | 172.3 |
| Sodium stearyl fumarate | 2.7 |
| Sum | 180 |

Linagliptin and anhydrous calcium hydrogen phosphate are dry mixed in a rotary drum mixer for about 10 min. The sodium stearyl fumarate is added and the components are mixed for about 1 min in a rotary drum mixer. The mixture is finally compressed into tablet cores using a Kilian rotary tablet press.

Example 9

| Ingredient | Amount (mg/tablet) |
| --- | --- |
| Linagliptin | 5.0 |
| Anhydrous calcium hydrogen phosphate | 172.3 |
| Magnesium stearate | 2.7 |
| Sum | 180 |

Linagliptin and anhydrous calcium hydrogen phosphate are dry mixed in a rotary drum mixer for about 10 min. The magnesium stearate is added and the components are mixed for about 1 min in a rotary drum mixer. The mixture is finally compressed into tablet cores using a Kilian rotary tablet press.

Example 10

| Ingredient | Amount (mg/tablet) |
| --- | --- |
| Linagliptin | 5.0 |
| Anhydrous calcium hydrogen phosphate | 67.3 |
| Mannitol | 105.0 |
| Sodium stearyl fumarate | 2.7 |
| Sum | 180 |

Linagliptin, anhydrous calcium hydrogen phosphate and mannitol are dry mixed in a rotary drum mixer for about 10 min. The sodium stearyl fumarate is added and the components are mixed for about 1 min in a rotary drum mixer. The mixture is finally compressed into tablet cores using a Kilian rotary tablet press.

Example 11

| Ingredient | Amount (mg/tablet) |
| --- | --- |
| Linagliptin | 5.0 |
| Anhydrous calcium hydrogen phosphate | 67.3 |
| Mannitol | 105.0 |
| Magnesium stearate | 2.7 |
| Sum | 180 |

Linagliptin, anhydrous calcium hydrogen phosphate and mannitol are dry mixed in a rotary drum mixer for about 10 min. The magnesium stearate is added and the components are mixed for about 1 min in a rotary drum mixer. The mixture is finally compressed into tablet cores using a Kilian rotary tablet press.

Example 12

9.7 mg Hydroxypropyl methylcellulose, 2.4 mg polyethylene glycol 6000, 0.875 mg talc, 2.1 mg titanium dioxide and 0.015 mg iron oxide are suspended in 25 g water at ambient temperature to produce a coating suspension. The tablet cores prepared in Examples 1 to 11 are coated with the coating suspension in a pan-coater to a weight gain of 5 mg/tablet to produce coated tablets.

When the tablets of Examples 1 to 12 are subjected to a dissolution test according to the Paddle method described in the European Pharmacopoeia 8.0 chapter 2.9.3 in a test volume of 900 ml in the test medium 0.01 M HCl at a stirring speed of 50 rpm using a Sotax AP 825 device with a photometer (wavelength 228 nm), not less than 90% of the active ingredient is dissolved within 10 minutes, and not less than 95% of the active ingredient is dissolved within 15 minutes.

When the tablets of Examples 1 to 12 are subjected to the content uniformity test described in the European Pharmacopoeia 8.0 chapter 2.9.40 (number of samples=10), the requirements for dosage uniformity are met (the acceptance value of the first 10 dosage units is less than or equal to L1 percent).

When the tablet hardness of the tablets of Examples 1 to 11 is determined according to the European Pharmacopoeia 8.0 chapter 2.9.8 (resistance to crushing of tablets) with the apparatus Schleuniger Typ 6D 4.11/6D 4.50, wherein the tablets are placed between the jaws in a manner that the force applies to the longest axis of the tablets, where applicable, the tablet hardness is in the range of from 60 to 120 N.

Example 13

| Ingredient | Amount (mg/tablet) |
| --- | --- |
| Linagliptin | 20.0 |
| Anhydrous calcium hydrogen phosphate | 58.0 |
| Sodium starch glycolate | 20.0 |
| Sodium stearyl fumarate | 2.0 |
| Sum | 100 |

Linagliptin, anhydrous calcium hydrogen phosphate and sodium starch glycolate are sieved through a 0.8 mm sieve and dry mixed in a Turbula mixer for about 10 min. The sodium stearyl fumarate is sieved through a 0.5 mm sieve, added to the mixture of the remaining components and all the components are mixed for about 1 min. The mixture is finally compressed into tablet cores using a rotary tablet press.

Example 14 (Comparative Example)

| Ingredient | Amount (mg/tablet) |
| --- | --- |
| Linagliptin | 20.0 |
| Microcrystalline cellulose (Avicel PH102) | 54.5 |
| Sodium starch glycolate | 20.0 |
| Silicon dioxide (Aerosil) | 0.5 |
| Sucralose | 1.0 |
| Lemon flavor | 2.0 |
| Sodium stearyl fumarate | 2.0 |
| Sum | 100 |

Linagliptin, microcrystalline cellulose, sodium starch glycolate, sucralose and the lemon flavor are sieved through a 0.8 mm sieve and dry mixed in a Turbula mixer for about 10 min. The silicon dioxide and sodium stearyl fumarate are sieved through a 0.5 mm sieve, added to the mixture of the remaining components and all the components are mixed for about 3 min. The mixture is finally compressed into tablet cores using a rotary tablet press.

When comparing the preparation process of the tablets of Example 13 and Comparative Example 14, it was noted that the flowability of the tabletting mass according to Comparative Example 14 was unsatisfactory resulting in an unstable tabletting process giving tablets having an unacceptable fluctuation in tablet weight and tablet hardness as shown in the table below:

| Sample tablet | Tablet hardness [N] | Sample tablet | Tablet weight [mg] |
| --- | --- | --- | --- |
| 1 | 68.0 | 1 | 99.1 |
| 2 | 68.9 | 2 | 100.5 |
| 3 | 67.3 | 3 | 103.9 |
| 4 | 69.5 | 4 | 101.0 |
| 5 | 79.4 | 5 | 108.2 |
| 6 | 56.4 | 6 | 99.6 |
| 7 | 47.3 | 7 | 94.9 |
| 8 | 76.2 | 8 | 99.0 |
| 9 | 56.6 | 9 | 95.5 |
| 10 | 93.6 | 10 | 105.4 |
| Mean | 68.3 | Mean | 100.71 |
| Max | 93.6 | Max | 94.9 |
| Min | 47.3 | Min | 108.2 |
| Max − Min | 46.3 | Max − Min | 13.3 |

By way of contrast, the tabletting mass of Example 13 according to the invention showed no flowability problems and could be processed without any difficulties. As a consequence, the tablet hardness and the tablet weight varied within an acceptable range as shown in the table below:

| Sample tablet | Tablet hardness [N] | Sample tablet | Tablet weight [mg] |
|---|---|---|---|
| 1 | 64.1 | 1 | 99.2 |
| 2 | 49.1 | 2 | 100.8 |
| 3 | 54.0 | 3 | 102.2 |
| 4 | 61.2 | 4 | 103.9 |
| 5 | 55.8 | 5 | 99.6 |
| 6 | 60.0 | 6 | 104.2 |
| 7 | 57.4 | 7 | 103.0 |
| 8 | 54.5 | 8 | 102.6 |
| 9 | 56.6 | 9 | 100.8 |
| 10 | 49.9 | 10 | 99.2 |
| Mean | 56.3 | Mean | 101.55 |
| Max | 64.1 | Max | 99.2 |
| Min | 49.1 | Min | 104.2 |
| Max – Min | 15.0 | Max – Min | 5.0 |

Dissolution tests with 3 tablets prepared according to Comparative Example 14 and 3 tablets prepared according to inventive Example 13 showed that complete dissolution was obtained after 15 minutes for all tablets analysed.

| Time [min] | Dissolution (mean value of 3 tablets prepared according to Example 13) [%] | Dissolution (mean value of 3 tablets prepared according to Comparative Example 14) [%] |
|---|---|---|
| 15 | 99 | 100 |
| 30 | 104 | 101 |
| 60 | 105 | 101 |

Example 15

| Ingredient | Amount (mg/tablet) |
|---|---|
| Linagliptin | 5.0 |
| Anhydrous calcium hydrogen phosphate | 166.9 |
| Kollidon CL (crospovidone) | 5.4 |
| Magnesium stearate | 0.69 |
| Sum | 177.99 |

Linagliptin, anhydrous calcium hydrogen phosphate and crospovidone are sieved through a 0.8 mm sieve and dry mixed in a Turbula mixer for about 10 min. The magnesium stearate is sieved through a 0.5 mm sieve, added to the mixture of the remaining components and all the components are mixed for about 1 min. The mixture is finally compressed into tablet cores using a rotary tablet press.

Example 16 (Comparative Example)

| Ingredient | Amount (mg/tablet) |
|---|---|
| Linagliptin | 5.0 |
| Mannitol (Pearlitol 160C) | 166.9 |
| Kollidon VA64 (copovidone) | 5.4 |
| Magnesium stearate | 0.69 |
| Sum | 177.99 |

5.4 g Copovidone (Kollidon VA64, Luviskol), 5.0 g linagliptin and 50.0 g mannitol are dry mixed in a rotary drum mixer for about 10 min to produce a pre-mix. The pre-mix is milled for about 10 min with a pin mill. 116.9 g Mannitol is added to the pre-mix, and mixed for about 10 min in a rotary drum mixer. This compacted mixture is compacted on a roller compactor. The compacted mixture is passed through a 1.0 mm sieve. 0.69 g Magnesium stearate is added and the components are mixed for about 1 min in a rotary drum mixer. The mixture is finally compressed into tablet cores using a rotary tablet press.

The content uniformity of the tablets obtained by Example 15 and by Comparative Example 16 has been determined according to the European Pharmacopoeia 8.0 chapter 2.9.40:

| Example 15 | | Comparative Example 16 | |
|---|---|---|---|
| Sample tablet | Assay [%] | Sample tablet | Assay [%] |
| 1 | 95.831 | 1 | 91.798 |
| 2 | 104.340 | 2 | 85.534 |
| 3 | 95.020 | 3 | 89.447 |
| 4 | 101.098 | 4 | 89.849 |
| 5 | 105.331 | 5 | 86.698 |
| 6 | 100.302 | 6 | 86.721 |
| 7 | 95.751 | 7 | 90.398 |
| 8 | 97.546 | 8 | 92.190 |
| 9 | 101.882 | 9 | 88.797 |
| 10 | 99.697 | 10 | 86.112 |
| Mean | 99.7 | | 88.8 |
| Min | 95.0 | | 85.5 |
| Max | 105.3 | | 92.2 |
| Acceptance value | 8.7 | Acceptance value | 15.5 |

While the tablets prepared according to Example 15 have an acceptance value of 8.7 and thus conform to the European Pharmacopoeia (the requirement for dosage uniformity is met), the tablets prepared according to Comparative Example 16 having an acceptance value of 15.5 do not conform to the European Pharmacopoeia (the requirement for dosage uniformity is not met).

The invention claimed is:

1. Pharmaceutical composition which is a tablet and has a tablet hardness in the range of from 60 to 120 N comprising linagliptin or a pharmaceutically acceptable salt thereof as active ingredient, wherein the pharmaceutical composition does not comprise a binder selected from the group consisting of lactose, povidone, copovidone, hydroxypropyl methylcellulose, hydroxypropylcellulose, pre-gelatinized starch, microcrystalline cellulose, polyethylene glycol and pullulan, and wherein the pharmaceutical composition is obtained by direct compression; wherein anhydrous calcium hydrogen phosphate is the only diluent present in the composition or wherein the diluent is a combination of anhydrous calcium hydrogen phosphate and mannitol.

2. Pharmaceutical composition according to claim 1 comprising additionally one or more excipients selected from diluents, disintegrants and lubricants.

3. Pharmaceutical composition according to claim 2, wherein the one or more excipients comprise diluents, wherein the diluents comprise anhydrous calcium hydrogen phosphate.

4. Pharmaceutical composition according to claim 1, wherein anhydrous calcium hydrogen phosphate and mannitol are the only diluents present in the composition.

5. Pharmaceutical composition according to claim 2, wherein the one or more excipients comprise lubricants, wherein the lubricants are selected from magnesium stearate, talc, stearic acid, calcium behenate, calcium stearate and sodium stearyl fumarate.

6. Pharmaceutical composition according to claim 2, wherein the one or more excipients comprise disintegrants, wherein the disintegrants are selected from starch, crospovidone, sodium starch glycolate and croscarmellose sodium.

7. Pharmaceutical composition according to claim 1, wherein the pharmaceutical composition does not comprise a binder and does not comprise a disintegrant and wherein the pharmaceutical composition is obtained by direct compression.

8. Pharmaceutical composition according to claim 1, which is in the form of a tablet, a coated tablet, an effervescent tablet, an orally disintegrating tablet, a chewable tablet or a capsule filled with minitablets.

9. Pharmaceutical composition according to claim 8, wherein the coating of the coated tablet comprises hydroxypropyl methylcellulose, polyethylene glycol, talc, titanium dioxide, and optionally a colorant.

10. Pharmaceutical composition according to claim 1, wherein the linagliptin is present as amorphous linagliptin, crystalline linagliptin having polymorphic form A, crystalline linagliptin having polymorphic form B and/or crystalline linagliptin having polymorphic form C.

11. Pharmaceutical composition according to claim 10, wherein the linagliptin is present as a mixture of crystalline linagliptin having polymorphic form A and crystalline linagliptin having polymorphic form B.

12. Process for preparing a pharmaceutical composition according to claim 1, comprising:
   I) blending linagliptin, or a pharmaceutically acceptable salt thereof, and the excipients, except the lubricant;
   II) lubricating the blend using the lubricant;
   III) directly compressing the blend;
   IV) optionally, applying a coating.

13. Pharmaceutical composition according to claim 1, wherein the linagliptin is present as amorphous linagliptin, crystalline linagliptin having polymorphic form A, crystalline linagliptin having polymorphic form B and/or crystalline linagliptin having polymorphic form C.

14. Pharmaceutical composition according to claim 4, wherein the linagliptin is present as amorphous linagliptin, crystalline linagliptin having polymorphic form A, crystalline linagliptin having polymorphic form B and/or crystalline linagliptin having polymorphic form C.

15. Pharmaceutical composition according to claim 7, wherein the linagliptin is present as amorphous linagliptin, crystalline linagliptin having polymorphic form A, crystalline linagliptin having polymorphic form B and/or crystalline linagliptin having polymorphic form C.

16. Process for preparing a pharmaceutical composition according to claim 4, comprising:
   I) blending linagliptin, or a pharmaceutically acceptable salt thereof, and the excipients, except the lubricant;
   II) lubricating the blend using the lubricant;
   III) directly compressing the blend;
   IV) optionally, applying a coating.

17. Process for preparing a pharmaceutical composition according to claim 7, comprising:
   I) blending linagliptin, or a pharmaceutically acceptable salt thereof, and the excipients, except a lubricant;
   II) lubricating the blend using the lubricant;
   III) directly compressing the blend;
   IV) optionally, applying a coating.

* * * * *